United States Patent [19]

Effland et al.

[11] Patent Number: 4,996,205
[45] Date of Patent: Feb. 26, 1991

[54] COMPOSITION AND METHOD OF USE OF PYRIDO[3,4-F]PYRROLO[1,2-B][1,2,5]TRIAZEPINES

[75] Inventors: Richard C. Effland, Bridgewater; Larry Davis, Sergentsville; Kevin J. Kapples, Little York; Gordon E. Olsen, Somerset, all of N.J.

[73] Assignee: Hoechst-Roussel Pharmaceuticals Inc., Somerville, N.J.

[21] Appl. No.: 468,402

[22] Filed: Jan. 19, 1990

Related U.S. Application Data

[62] Division of Ser. No. 397,922, Aug. 24, 1989, Pat. No. 4,914,103, which is a division of Ser. No. 223,847, Jul. 25, 1988, Pat. No. 4,879,382.

[51] Int. Cl.$^5$ ............................................. A01N 43/58
[52] U.S. Cl. ...................................................... 514/250
[58] Field of Search .......................................... 514/250

Primary Examiner—Stanley J. Friedma
Assistant Examiner—Theodore J. Criares
Attorney, Agent, or Firm—Tatsuya Ikeda; Karen E. Klumas

[57] ABSTRACT

Pyrido[3,4-f]pyrrolo[1,2-b][1,2,5]triazepines and methods for treating depression, alleviating pain and inflammation, and enhancing memory utilizing compounds or compositions thereof are disclosed.

4 Claims, No Drawings

COMPOSITION AND METHOD OF USE OF PYRIDO[3,4-F]PYRROLO[1,2-B][1,2,5]TRIAZEPINES

This is a division of prior application Ser. No. 397,922, filed Aug. 24, 1989, now U.S. Pat. No. 4,914,103, which is a division of prior application Ser. No. 223,847, filed July 25, 1988, now U.S. Pat. No. 4,879,382.

This invention relates to pyrido[3,4-f]pyrrolo[1,2-b][1,2,5]triazepines of the formula:

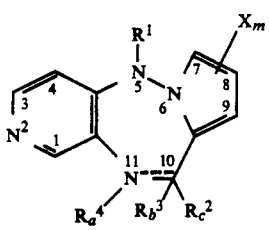

FORMULA I wherein $R^1$ is loweralkyl, arylloweralkyl or aminoloweralkyl; $R^2$ is hydrogen, loweralkyl, arylloweralkyl, aminoloweralkyl, aryl or a group of the formula

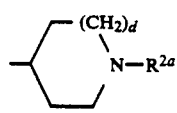

wherein d is an integer having a value of zero or 1 and $R^{2a}$ is hydrogen, loweralkyl, arylloweralkyl or aminoloweralkyl; $R^3$ is hydrogen or loweralkyl, or together with $R^2$ constitutes a radical of the formula =O; $R^4$ is hydrogen, loweralkyl, arylloweralkyl, aminoloweralkyl, formyl, loweralkylcarbonyl, aminocarbonyl, arylaminocarbonyl, or a group of the formula

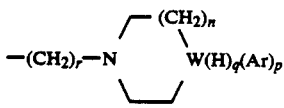

wherein W is carbon or nitrogen, Ar is aryl, q is an integer having a value from zero to 2, inclusive, p is an integer having a value of zero or 1, with the proviso that the sum of p and q is 1 when W is nitrogen and 2 when W is carbon, n is an integer having a value of zero or 1, and r is an integer having a value from 2 to 4, inclusive; X is halogen, loweralkyl, loweralkenyl, formyl or loweralkanol; m is an integer having a value of zero or 1; the dotted line is an optional bond; and a, b, and c, are integers having values of zero or one with the proviso that in the presence of said optional bond a is zero and the sum of b plus c is one, and in the absence of said optional bond a, b, and c each have a value of 1; which compounds, alone or in combination with one or more pharmaceutically acceptable carriers, are useful as antidepressant, antiinflammatory, analgesic, and memory enhancing agents.

Throughout the specification and appended claims a given formula or name shall encompass the stereo, optical, and geometrical isomers thereof, as well as the pharmaceutically acceptable acid addition salts and solvates (e.g., hydrates) of same.

Subgeneric to the pyrido[3,4-f]pyrrolo[1,2-b][1,2,5]triazepines of this invention are formula I compounds wherein (a) $R^1$ is loweralkyl;
(b) $R^1$ is arylloweralkyl;
(c) $R^1$ is aminoloweralkyl;
(d) $R^2$ is hydrogen;
(e) $R^2$ is loweralkyl;
(f) $R^2$ is arylloweralkyl;
(g) $R^2$ is aminoloweralkyl;
(h) $R^2$ is aryl;
(i) $R^2$ is a group of the formula:

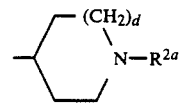

wherein d is an integer having a value of zero or 1 and $R^{2a}$ is hydrogen, loweralkyl, arylloweralkyl or aminoloweralkyl;
(j) $R^3$ is hydrogen;
(k) $R^3$ is loweralkyl;
(l) $R^2$ and $R^3$ consititute a radical of the formula =O;
(m) $R^4$ is hydrogen;
(n) $R^4$ is loweralkyl;
(o) $R^4$ is arylloweralkyl;
(p) $R^4$ is aminoloweralkyl;
(q) $R^4$ is loweralkylcarbonyl, aminocarbonyl, or arylaminocarbonyl;
(r) $R^4$ is a group of the formula:

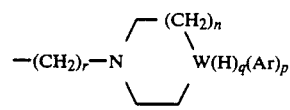

wherein W is carbon or nitrogen; Ar is aryl; q is an integer having a value from zero to 2, inclusive; p is an integer having a value of zero or 1, with the proviso that the sum of p and q is 1 when W is nitrogen and 2 when W is carbon; n is an integer having a value of zero or 1; and r is an integer having a value from 2 to 4, inclusive;
(s) $R^4$ is a group of the formula:

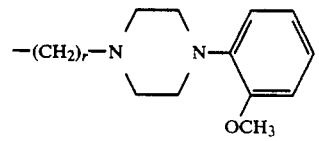

wherein r is an integer having a value from 2 to 4, inclusive; and
(t) m is zero.

Unless otherwise stated or indicated, the following definitions shall apply throughout the specification and the appended claims.

The term "loweralkyl" shall mean a linear or branched, acyclic hydrocarbon radical containing no unsaturation and having the formula $-C_xH_{2x+1}$ wherein x is an integer having a value of 1 to 7 inclusive, such as methyl, ethyl, 1-propyl, 2-propyl, 1-butyl, 1-pentyl, 2-pentyl, 3-hexyl, 4-heptyl, and the like.

The term "loweralkoxy" shall mean an acyclic organic radical of the formula $-OC_xH_{2x+1}$ wherein x is an integer having a value of 1 to 7, inclusive, such as methoxy, ethoxy, 1- and 2-propoxy, 1,2-dimethylethoxy, 1-butoxy, 1- and 2-pentoxy, 3-hexoxy, 4-heptoxy, and the like.

The term "aryl" shall mean a phenyl group optionally substituted by one or more substituents selected from the group consisting of halogen, loweralkyl, loweralkoxy, and trifluoromethyl.

The term "arylloweralkyl" shall mean a loweralkyl group having an aryl substituent thereon.

The term "amino" shall mean a group of the formula —$NR^5R^6$ wherein $R^5$ and $R^6$ are independently hydrogen or loweralkyl;

The term "arylamino" shall mean an amino group substituted at the nitrogen atom thereof by an aryl group.

The term "aminocarbonyl" shall mean a group of the formula —$C(O)NR^5R^6$ wherein $R^5$ and $R^6$ are independently hydrogen or loweralkyl.

The term "aminoloweralkyl" shall mean a loweralkyl group having an amino substituent thereon.

The term "loweralkylcarbonyl" shall mean a group of the formula —$C(O)C_xH_{2x+1}$ wherein x is an integer having a value of 1 to 7, inclusive.

The term "loweralkoxycarbonyl" shall mean a group of the formula —$C(O)OC_xH_{2x+1}$ wherein x is an integer having a value of 1 to 7, inclusive.

The term "arylaminocarbonyl" shall mean an amino carbonyl group substituted at the nitrogen atom thereof by an aryl group.

The term "halogen" shall mean a member of the group consisting of fluorine, chlorine, bromine and iodine radicals.

The term "loweralkenyl" shall means a linear or branched, acyclic hydrocarbon radical having one olefinic bond and represented by the formula —$C_xH_{2x+1}$ wherein x is an integer having a value of 3 to 7, inclusive, such as 2-propenyl, 3-butenyl, 3-pentenyl, 3-hexenyl, 6-heptenyl, and the like.

The term "loweralkanol" shall mean a loweralkyl group having an hydroxy substituent, such as methanol, ethanol, 1- and 2-propanol, 2,2-dimethylethanol, pentanol, hexanol, heptanol, and the like.

The pyrido[3,4-f]pyrrolo[1,2-b][1,2,5]triazepines of this invention are synthesized by the processes illustrated in the Reaction Scheme which follows.

To prepare the parent system i.e., a 5-alkyl-5H-pyrido[3,4-f]pyrrolo[1,2-b][1,2,5]triazepine 7, an N-(substituted)amino pyrrole 4 is reacted with 4-chloro-3-nitropyridine (see Talik, T. et al., Rocz. Chem., 1967, 43(5), 923–34 for the synthesis of same) to produce an N-substituted-N-(1H-pyrrol-1-yl)-3-nitropyridinamine 5 which is converted to the corresponding carboxaldehyde derivative 6 and then cyclized.

As illustrated in the Reaction Scheme the N-(substituted) aminopyrrole 4 is produced by reacting N-aminopyrrole 1 with ethyl chloroformate to form a secondary carbamate derivative 2 which is converted to a tertiary carbamate derivative 3 by reaction with an alkyl-, benzyl or aminoalkylhalide (e.g., methyl iodide, ethyl iodide, ethyl bromide, benzyl bromide, dimethylaminopropyl chloride, and the like), and then hydrolyzed. The hydrolysis of the tertiary carbamate derivative 3 is ordinarily conducted in the presence of an alkali metal hydroxide at temperatures of from about 25° C. to reflux; reflux temperatures being preferred.

The reaction of the N-(substituted)amino pyrrole 4 with 4-chloro-3-nitropyridine is conducted at a temperature of from about 20° C. to about 100° C., preferably from about 20° C. to about 60° C., in a suitable organic solvent e.g., polar aprotic solvents such as dimethylsulfoxide, hexamethylphosphoramide, dimethylacetamide, dimethylformamide, and the like; dimethylformamide, being preferred.

To generate the corresponding carboxaldehyde derivative 6, the N-substituted-N-(1H-pyrrol-1-yl)-3-nitro-4-pyridinamine 5 is reacted with phosphorous oxychloride and dimethylformamide in the presence of a suitable solvent at a temperature of from about 20° C. to about 100° C. Suitable solvents for this reaction include halogenated hydrocarbons such as for example, dichloromethane, dichloroethane, chloroform, and the like; dichloroethane being preferred.

Cyclization of the 1-[N-substituted-N-(3-nitro-4-pyridinyl)amino] pyrrole-2-carboxaldehyde 6 is accomplished by a variety of mechanisms wherein the 3-nitro group of the aldehyde 6 is reduced, forming an 1-[N-substituted-N-(3-amino-4-pyridinyl)amino]pyrrole-2-carboxaldehyde intermediate 6a which undergoes intramolecular condensation to afford the the parent system 7. In general, the reduction/intramolecular condensation proceeds without isolation of the amino substituted intermediate 6a. Reduction of the carboxaldehyde derivative 6 can be accomplished by any of several methods including catalytic reduction (e.g., reaction with hydrogen in the presence of a suitable catalyst such as, for example, palladium, platinum, and the like at a pressure of from about 25 psi to about 50 psi and a temperature of from about 10° C. to about 80° C.) or treatment with an appropriate reducing agent (e.g. a metal-acid combination such as, for example, stannous chloride or ferrous chloride, in the presence of a suitable mineral acid) at a temperature of from about 0° C. to about 80° C. Cyclization of the carboxaldehyde derivative 6 is preferably achieved by treatment with stannous chloride and hydrochloric acid at a temperature of from about 0° C. to about 15° C., in the presence of a suitable organic solvent such as tetrahydrofuran and dioxane, tetrahydrofuran being preferred.

As further illustrated in the Reaction Scheme, reduction of the parent 5-substituted-5H-pyrido[3,4-f]pyrrolo[1,2-b][1,2,5]triazepine 7 affords the corresponding 10,11-dihydro-5-substituted-5H-pyrido[3,4-f]pyrrolo[1,2-b][1,2,5]triazepine 8 from which a variety of 11-substituted derivatives 9 are produced.

Reduction of the parent system 7 is conveniently accomplished by treatment with a suitable reducing agent (e.g., alkali metal borohydrides such as lithium borohydride, potassium borohydride, sodium borohydride, and the like). The reaction is typically carried out in an alkanol (e.g. methanol, ethanol, 1- and 2-propanol, and the like, ethanol being preferred) at a temperature of from about 0° C. to about 100° C., preferably from about 20° C. to about 30° C.

As further illustrated by the Reaction Scheme, the reaction of a Grignard reagent $R^2$MgHal (wherein $R^2$ is loweralkyl, arylloweralkyl, aminoloweralkyl, aryl, or a group of the formula

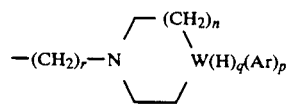

as previously described and Hal is chlorine or bromine) with the parent 5-substituted-5H-pyrido[3,4-f]pyrrolo[1,2-b] [1,2,5]triazepine 7 yields a variety of 10-substituted derivatives 10. The Grignard reaction is generally conducted at a temperature of from about 0° C. to about 100° C., preferably from about 5° C. to about 60° C., in the presence of an organic solvent. Suitable solvents include ethers such as diethyl ether, dioxane, tetrahydrofuran, and the like; tetrahydrofuran being preferred.

Substitution at the 11-position of the 10,11-dihydro derivative 8 or 10 is achieved by a variety of reactions tailored to the particular functional group $R^4$. For example, to provide a 10,11-dihydro-5H-pyrido[3,4-f]pyrrolo[1,2-b][1,2,5]triazpine wherein $R^4$ is aminocarbonyl or arylaminocarbonyl the 10,11-dihydro derivative 8 or 10 is reacted with an isocyanate of the formula O=C=NR$^{4a}$ (wherein R$^{4a}$ is loweralkyl or aryl) at a temperature of from about 0° C. to about 80° C. in an appropriate organic solvent (e.g. hydrocarbons such as benzene, xylene, toluene and the like; benzene being preferred).

Loweralkylcarbonyl functionality can be introduced at the 11-position of the 10,11-dihydro derivative 8 or 10 by reaction with an acid anhydride of the formula R$^{4a}$C(O)OC(O)R$^{4a}$ wherein R$^{4a}$ is loweralkyl (e.g., acetic anhydride). The acetylation is generally conducted at a temperature of from about 0° C. to about 55° C., preferably from about 0° C. to about 30° C. to give a variety of 11-substituted derivatives 9 or 11.

Treatment of the 10,11-dihydro derivatives 8 or 10 with a halide of the formula $R^4$Hal wherein $R^4$ is loweralkyl, arylloweralkyl or aminoloweralkyl and Hal is halogen provides a convenient means of synthesizing derivatives 9 or 11 having the desired functional group $R^4$ at the 11-position thereof. The reaction is generally conducted at a temperature of from about 20° C. to about 80° C.; optimal reaction temperatures are however, subject to variation depending upon the particular solvent employed. Suitable solvents for the reaction include polar aprotic solvents (e.g., dimethyl sulfoxide or dimethylformamide); dimethylformamide being preferred. The reaction is generally carried out in the presence of an acid acceptor (e.g. tertiary amines, alkali metal carbonates and bicarbonates, and the like, such as, for example, triethylamine, potassium carbonate, sodium carbonate, sodium bicarbonate, and the like). If desired, a promotor such as, for example, potassium iodide, may also be present.

REACTION SCHEME #1

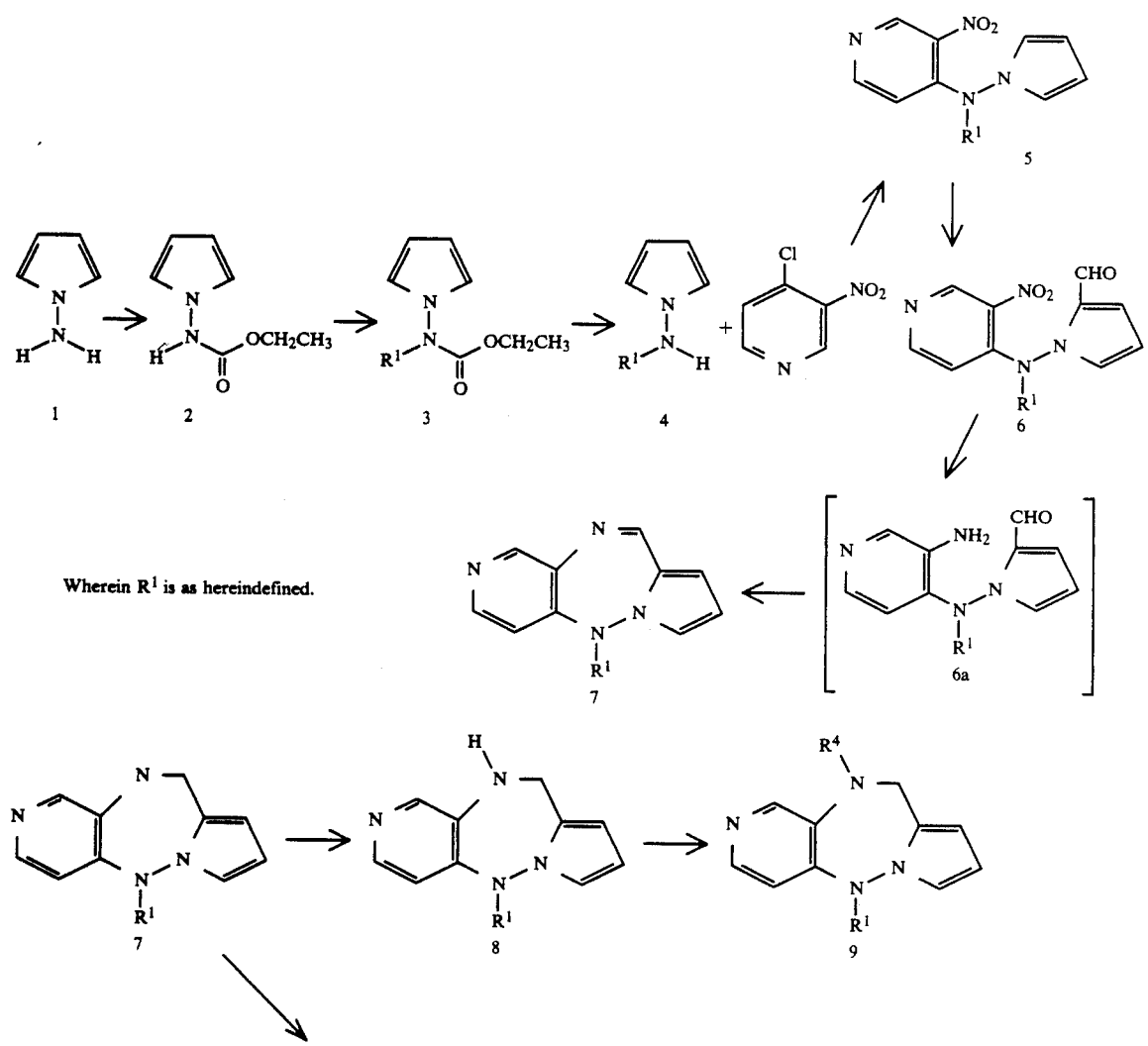

Wherein $R^1$ is as hereindefined.

-continued
REACTION SCHEME #1

Wherein $R^1$, $R^2$ and $R^4$ are as hereindefined.

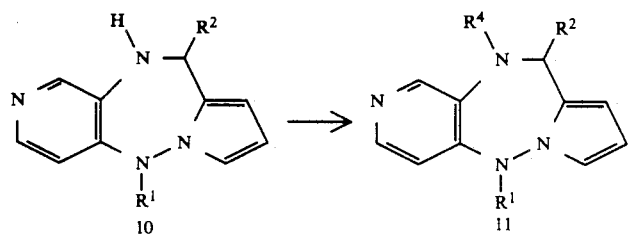

REACTION SCHEME 2

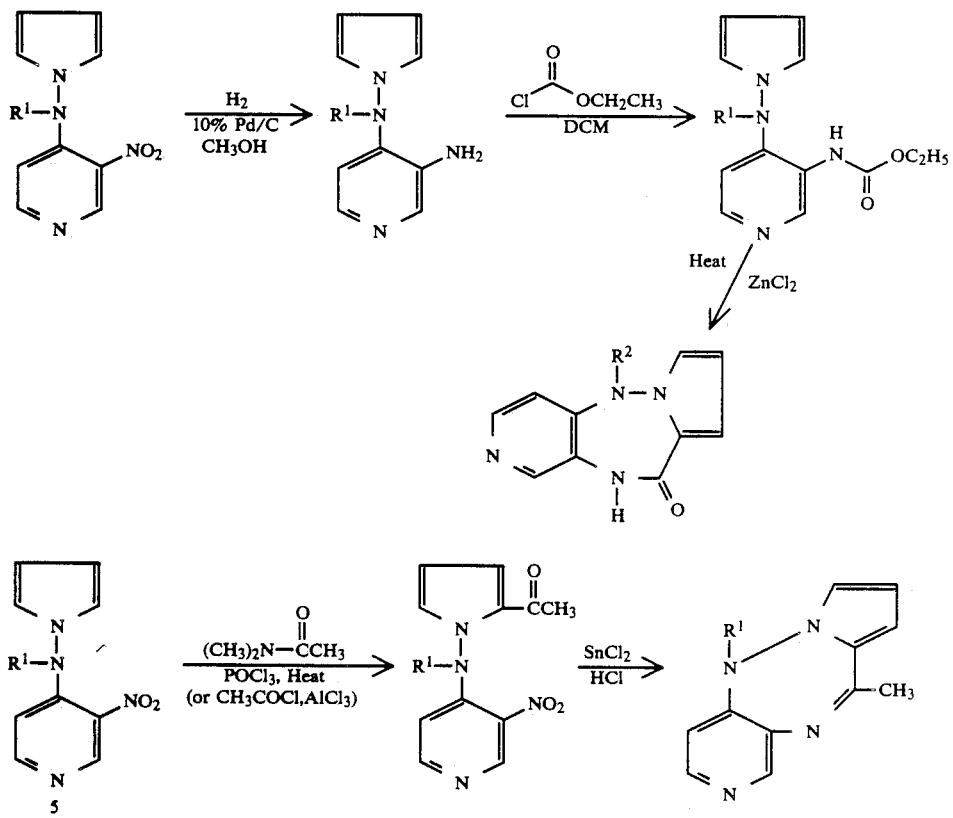

Included among the compounds of this invention are:
5-benzyl-10,11-dihydro-5H-pyrido[3,4-f]pyrrolo[1,2-b][1,2,5]triazepine;
10,11-dihydro-5-[3-(N,N-dimethylamino)propyl]-5H-pyrido[3,4-f]pyrrolo[1,2-b][1,2,5]triazepine;
11-carbamoyl-5-methyl-10,11-dihydro-5H-pyrido[3,4-f]pyrrolo[1,2-b][1,2,5]triazepine;
5-benzyl-11-carbaniloyl-10,11-dihydro-5H-pyrido[3,4-f]pyrrolo[1,2-b][1,2,5]triazepine;
5-benzyl-10,11-dihydro-11-methoxycarbonyl-5H-pyrido[3,4-f]pyrrolo[1,2-b][1,2,5]triazepine;
10,11-dihydro-7-ethyl-5-methyl-5H-pyrido[3,4-f]pyrrolo[1,2-b][1,2,5]triazepine;
7-chloro-10,11-dihydro-5-methyl-5H-pyrido[3,4-f]pyrrolo[1,2-b][1,2,5]triazepine;
10-benzyl-10,11-dihydro-5-methyl-5H-pyrido[3,4-f]pyrrolo[1,2-b][1,2,5]triazepine;
10-[1-(benzyl)piperidin-4-yl]-10,11-dihydro-5-methyl-5H-pyrido[3,4-f]pyrrolo[1,2-b][1,2,5]triazepine;
10,11-dihydro-5-methyl-10-oxo-5H-pyrido[3,4-f]pyrrolo[1,2-b][1,2,5]triazepine;
10,11-dihydro-5,10,10-trimethyl-5H-pyrido[3,4-f]pyrrolo[1,2-b][1,2,5]triazepine;
11-carbaniloyl-10,11-dihydro-5-methyl-5H-pyrido[3,4-f]pyrrolo[1,2-b][1,2,5]triazepine;
11-benzyl-10,11-dihydro-5-methyl-5H-pyrido[3,4-f]pyrrolo[1,2-b][1,2,5]triazepine;
10,11-dihydro-5-methyl-11-[3-(N,N-dimethylamino)propyl]-5H-pyrido[3,4-f]pyrrolo[1,2-b][1,2,5]triazepine;
10,11-dihydro-5,10-dimethyl-7-(1-propenyl)-5H-pyrido[3,4-f]pyrrolo[1,2-b][1,2,5]triazepine;
10,11-dihydro-5-[2-(N-methylamino)ethyl]-5H-pyrido[3,4-f]pyrrolo[1,2-b][1,2,5]triazepine;
5-benzyl-7-formyl-10,11-dihydro-5H-pyrido[3,4-f]pyrrolo[1,2-b][1,2,5]triazepine; and
10,11-dihydro-7-(hydroxymethyl)-5H-pyrido[3,4-f]pyrrolo[1,2-b][1,2,5]triazepine.

The compounds of this invention are useful as analgesic agents due to their ability to alleviate pain in mammals. The procedure employed to determine analgetic utility is a modification of the phenyl-p-quinone writhing assay in mice, a standard assay for analgetic activity [Proc. Soc. Exptl. Med., 95 729 (1957)]. Pursuant to the modified procedure phenyl-p-benzoquinone (Eastman, 12.5 mg) is dissolved in 5 ml of 95% ethanol and the solution is diluted to a total volume of 100 ml with distilled water. The solution is administered to the subject mice intraperitoneally at a dose of 10 ml per kg of body weight. A characteristic "writhe", an inward rotation of one or more feet with twisting and turning of the trunk, drawing in of the abdominal wall, lordosis and arching of the back, is produced.

A total of 28 male mice (Charles River, CD-1), weighing 18 to 30 grams, are employed for a time response. The subject animals receive food and water ad libitum. Test compounds are dissolved in distilled water, or suspended in distilled water containing one drop of a suitable surfactant, such as Tween-80.

Four groups of five animals (20 animals) are given the test compound subcutaneously (s.c.) or perorally (p.o.) at 15, 30, 45 and 60 minutes prior to administration of the phenyl-p-benzoquinone. A control group (2 animals per group) receive an equal volume of the vehicle. After the administration of the phenyl-p-benzoquinone, the mice are placed separately in one liter beakers, and after five minutes, are observed for ten minutes. The number of writhes for each animal is recorded. The following formula is used to compute the percent inhibition:

$$\frac{\bar{x} \text{ Writhes in Control Group} - \bar{x} \text{ Writhes in Drug Group}}{\bar{x} \text{ Writhes in Control Group}} \times 100$$

A dose range determination is run in the same manner as the time response except 10 animals per group are tested at the peak time of test drug activity. Fifty animals, 4 test drug groups, and a vehicle control are employed. Animals are dosed and tested in a randomized manner. The time period with the greatest percent of inhibition is considered the peak time.

The results of the phenyl-p-quinone writhing assay for several of the compounds of this invention are provided in Table 1.

TABLE 1

| Compound | Analgesic Activity % Inhibition of Writhing at a Screening Dose of 20 mg/kg, s.c. |
|---|---|
| 10,11-dihydro-5-methyl-5H-pyrido[3,4-f]pyrrolo[1,2-b]-[1,2,5]triazepine | 50%[1] |
| 10,11-dihydro-5-methyl-10-phenyl-5H-pyrido[3,4-f]pyrrolo[1,2-b]-[1,2,5]triazepine | 47% |
| 10,11-dihydro-5-methyl-10-[3-(N,N-dimethylamino)propyl]-5H-pyrido[3,4-f]pyrrolo[1,2-b]-[1,2,5]triazepine | 57% |
| 10,11-dihydro-5-methyl-11-methylcarbamoyl-5H-pyrido[3,4-f]pyrrolo[1,2-b]-[1,2,5]triazepine maleate | 44% |
| 10,11-dihydro-11-formyl-5-methyl-5H-pydrido[3,4-f]pyrrolo[1,2-b]-[1,2,5]triazepine maleate | 47% |

TABLE 1-continued

| Compound | Analgesic Activity % Inhibition of Writhing at a Screening Dose of 20 mg/kg, s.c. |
|---|---|
| Pentazocine | 50%[2] |

Analgesia production is achieved when the compounds of this invention are administered to a subject requiring such treatment at an effective oral, parenteral or intravenous dose of from 1 to 300 mg/kg of body weight per day. Compounds which achieve effective analgesia production at doses of from about 1 to about 100 mg/kg of body weight per day are particularly desirable. It is to be understood, however, that for any particular subject, specific dosage regimens should be adjusted according to the individual need and the professional judgment of the person administering or supervising the administration of the aforesaid compound. It is further understood that the dosages set forth herein are exemplary only and that they do not, to any extent, limit the scope or practice of the invention.

Several of the compounds of this invention have utility as antiinflammatory agents. Antiinflammatory activity was measured pursuant to the adjuvant-induced polyarthritis syndrome in rats assay by a procedure similar to that described by C. M. Pearson and F. D. Wood, Arthritis and Rheumatism, 2, 440 (1959).

Groups of 10 male Charles River-Wistar Lewis rats weighing 150 to 175 g were individually housed and maintained on a regular rat chow diet. Water was given ad libitum. The adjuvant was prepared by suspending 75 mg of *Mycobacterium butyricum* (Difco Laboratories, Detroit, Mich.) in 10 ml of white paraffin oil with continuous stirring for 2 hours at room temperature prior to administration. Test compounds are prepared by suspending the drug in water, adding one drop of Tween 80 per 10 ml of suspension, and homogenizing. The adjuvant suspension (0.1 ml) was injected into the foot-pad of the left hind paw of the rat. Test compound suspensions were administered orally (10 ml/kg) the day before adjuvant suspension injection and the administration was continued daily for 21 days. One group of ten rats was used for the test drug. Standard, adjuvant-injected control and non-injected control groups were run along with the test drug. Control animals received vehicle (10 ml/kg). Injected and non-injected paw volumes were determined on the day the adjuvant suspension was given, and on subsequent days thereafter (usually days 5, 10, 18, and 21) by the method of C. A. Winter, et al., Proc. Soc. Exp. Biol. Med., 111, 544 (1962).

The percent inhibition of paw volume (injected and non-injected paw) were calculated by the following formula:

% Inhibition =

$$\frac{\substack{\text{Mean Paw Volume} \\ \text{Change of Injected} \\ \text{(or Non-Injected) Control}} - \substack{\text{Mean Paw Volume} \\ \text{Change of Drug} \\ \text{Treated}}}{\text{Mean Paw Volume Change of Injected (or Non-Injected) Control}} \times 100$$

A calculated ED$_{50}$ i.e., the dose at which the test compound effects a 50% inhibition of adjuvant induced inflammation, is calculated by computer linear regression analysis.

The results of the adjuvant-induced polyarthritis syndrome test procedure for 10,11-dihydro-5-methyl-10-[(1-methyl)piperidin-4-yl]-5H-pyrido[3,4-f]pyrrolo[1,2-b][1,2,5]triazepine, a representative compound, is provided in Table 2.

TABLE 2

| Compound | Non-Injected Paw $ED_{50}$ mg/kg p.o. |
|---|---|
| 10,11-dihydro-5-methyl-10-[(1,methyl)piperidin-4-yl]-5H-pyrido[3,4-f]pyrrolo[1,2-b]-[1,2,5]triazepine | 53.7 |
| Aspirin | 110 |

Inflammation inhibition is achieved when the compounds of this invention are administered to a subject requiring such treatment at an effective oral, parenteral, or intravenous dose of from about 1 to about 300 mg/kg of body weight per day. Compounds which achieve effective inflammation inhibition at doses of from about 1 to about 100 mg/kg of body weight per day are particularly desirable. It is to be understood, however, that for any particular subject, specific dosage regimens should be adjusted according to the individual need and professional judgment of the person administering or supervising the administration of same. Doses set forth herein are exemplary only and are not intended to limit the scope or practice of the invention.

Several of the compounds of this invention are also useful as antidepressants by virtue of their ability to elicit an antidepressant response in mammals. Antidepressant activity is determined by the tetrabenazine induced ptosis assay in mice, [International Journal of Neuropharmacology, 8, 72 (1969]), a standard assay for the determination of antidepressant activity.

In the tetrabenazine induced ptosis assay, male mice (Charles River, CD-1), weighing 20 to 39 g, are used in test groups of five animals. Test compounds are dissolved, or suspended with 1 drop of Tween-80, in distilled water and administered to the animals in volumes of 10 cc per kg of body weight. Tetrabenazine methanesulfonate (76.78% as the free base) is dissolved in distilled water and the concentration of the solution is adjusted so that the dose, administered intraperitoneally (i.p.) to the animals, is 40 mg of tetrabenazine base per kg of animal body weight.

The test compound is administered intraperitoneally (i.p.) or orally to the subject animals, and the tetrabenazine solution is administered 30 minutes or 60 minutes, respectively, thereafter. Tetrabenazine solution and the solvent used to dissolve, or suspend, the test compounds are administered by the same route and at the same intervals as the test compounds to a control group.

The subject animals are placed in individual plastic containers (10½"×8"×6") thirty (i.p.) and sixty minutes (p.o.) after administration of the tetrabenazine solution, and one minute thereafter, the animals are scored for ptosis on the following scale:

| Eye Closure | Score |
|---|---|
| Eyes closed | 4 |
| Eyes ¾ closed | 3 |
| Eyes ½ closed | 2 |
| Eyes ¼ closed | 1 |

| Eye Closure | Score |
|---|---|
| Eyes open | 0 |

The total score for each group of 5 animals will therefore vary from 0 to 20; these scores are used as the indications of the activity of the test compound.

The vehicle-control group score is used as a determination of the validity of each test. The results are discarded and the test is repeated, if the control score is determined to be less than 17.

A dose range determination is generally reserved for those compounds which inhibit ptosis by greater than about 45–50% at the screening dose.

For calculation of the $ED_{50}$ value of a test compound; i.e., the calculated dose at which the test compound effects a 50% inhibition of tetrabenazine-induced ptosis, four or five doses are administered, and only vehicle-control scores of 17 to 20 are acceptable. A linear-regression analysis is used to estimate $ED_{50}$ values and 95% confidence limits.

The antidepressant activity of representative compounds is provided in Table 3.

TABLE 3

| Compound | Antidepressant Activity $ED_{50}$ mg/kg i.p. |
|---|---|
| 10,11-dihydro-5-methyl-10-[(1-methyl)piperidin-4-yl]-5H-pyrido[3,4-f]pyrrolo[1,2-b]-[1,2,5]triazepine | 15.7 |
| 10,11-dihydro-5,10-dimethyl-5H-pyrido[3,4-f]pyrrolo[1,2-b]-[1,2,5]triazepine | (47% inhibition of ptosis at a dose of 10 mg/kg i.p.) |
| amitryptyline | 1.5 |

Antidepressant activity is achieved when the compounds of this invention are administered to a subject requiring such treatment at an effective oral, parental or intravenous dose of from 1 to 100 mg/kg of body weight per day.

Some of the compounds of this invention are useful as memory enhancing agents. This utility is demonstrated by the ability of these compounds to restore cholinergically deficient memory in the dark avoidance assay. Pursuant to the dark avoidance assay, mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an antichlolinergic agent that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

The memory enhancing activity of representative compounds of this invention is provided in Table 4.

TABLE 4

| Compound | Dose | % of Animals With Scopolamine Induced Memory Deficit Reversed |
| --- | --- | --- |
| 10,11-dihydro-5,10-dimethyl-5H-pyrido-[3,4-f]pyrrolo[1,2-b]-[1,2,5]triazepine | 2.5 mg/kg s.c. | 33 |
| 10,11-dihydro-10-[3-(N,N-dimethylamino)propyl]-5-methyl-5H-pyrido-[3,4-f]pyrrolo[1,2-b]-[1,2,5]triazepine | 1.25 mg/kg s.c. | 27 |
| physostigmine | 0.31 mg/kg s.c. | 20 |

Memory enhancing activity is achieved when the compounds of this invention are administered to a subject requiring such treatment at an effective oral, parenteral or intravenous dose of from 1 to 100 mg/kg of body weight per day.

It is to be understood that the dosages set forth above with respect to analgesic, antiinflammatory, antidepressant and memory enhancing activity for any particular subject should be adjusted according to the individual need and the professional judgement of the person administering or supervising the administration of the aforesaid compound. It is further understood that the dosages set forth herein are exemplary only and that they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. The compounds of this invention, while effective themselves, may be formulated and administered in the form of their pharmaceutically acceptable acid addition salts for purposes of stability, convenience, increased solubility and the like. Preferred pharmaceutically acceptable acid addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, succinic acid, maleic acid and the like.

Effective quantities of the compounds of this invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0 and 300 milligrams of the active compound.

The tablets, pills, capsules, troches and the like may also contain the following ingredients: a binder such as microcrystalline cellulose, gum tragancanth or gelatin; an excipient such as starch or lactose, a disintegrating agent such as alginic acid, Promogel TM, cornstarch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring. When the dosage unit form is a capsule, it may contain, in addition to materials of the proceeding type, a liquid carrier such as a fatty oil. Other dosage unit forms may contain other various materials which modify the physical form of the dosage unit such as, for example, coatings. Thus, tablets or pills may be coated with sugar, shellac, or other enteric coating agents. A syrup may contain, in addition to the active compounds, sucrose and/or other sweetening agents, preservatives, dyes, coloring agents and/or flavorings. Materials used in preparing these various compositions should be pharmaceutically pure and nontoxic in the amounts used.

For the purpose of parenteral therapeutic administration, the active compounds of this invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 and 100 miligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as as ethylenediaminetetraacetic acid; buffers such as acetates, citrates or phosphates; and agents for the adjustment of tonicity such as sodium chloride or dextrose. The parenteral preparation can be enclosed in ampules, disposable syringes or multiple dose vials made of glass or plastic.

EXAMPLES

The following Examples are for illustrative purposes only and are not to be construed as limiting the invention.

EXAMPLE 1

5-Methyl-5H-pyrido[3,4-f]pyrrolo[1,2-b][1,2,5]triazepine

Step 1

A mixture of 15 g of sodium bicarbonate and 9.2 g of (N-amino)pyrrole in 50 ml of dichloromethane was treated over a period of fifteen minutes with 11.4 ml of ethyl chloroformate. The reaction mixture was then stirred at ambient temperature for four hours and filtered. The filtrate was washed with water followed by a saturated solution of sodium chloride, dried over anhydrous magnesium sulfate, and filtered. Concentration afforded 17 g of N-(1H-pyrrol-1-yl)carbamic acid ethyl ester, m.p. 60°-61° C.; MS(EI)M+@ 154 (100%); IR(CHCl$_3$)—NH @ 3430 cm$^{-1}$, C=O @ 1755 cm$^{-1}$.

Step 2

A cold solution of 9 g of the secondary carbamate of step 1 in 30 ml of tetrahydrofuran was treated with 7.8 g of potassium t-butoxide and then stirred at 5° C. for one hour. The mixture was then treated with a solution of 4.1 ml of methyl iodide in 10 ml of tetrahydrofuran and stirred at ambient temperature for four hours. The reaction mixture was then poured into 100 ml of water, stirred for five minutes, and extracted with ethyl acetate. The organic layer was washed with water followed by a saturated solution of sodium chloride, dried over anhydrous magnesium sulfate, and filtered. Concentration afforded 9.4 g of N-methyl-N-(1H-pyrrol-1-yl)carbamic acid ethyl ester as an oil; MS(EI)M+@ 168 (100%); IR(CHCl$_3$) C=O @ 1720 cm$^{-1}$.

Step 3

A solution of 9.4 g of the tertiary carbamate of step 2 in 15 ml of ethylene glycol was treated with 10 ml of a 50% aqueous solution of sodium hydroxide. After stirring at reflux for four hours, the reaction mixture was poured into 100 ml of water, stirred for a few minutes and then extracted with ethyl acetate. The organic layer was washed with water followed by a saturated solution of sodium chloride, dried over anhydrous magnesium sulfate, filtered and concentrated. Vacuum distillation of the resultant oil afforded 4.3 g of N-(methylamino)pyrrole as an oil, b.p. 32°-35° C. @ 1 mm Hg, MS(EI)M+@ 96 (100%), IR(CHCl$_3$)—NH @ 3340 cm$^{-1}$.

Step 4

A solution of 8.8 g of N-(methylamino)pyrrole and 14.5 g of 4-chloro-3-nitropyridine in 200 ml of dimethylformamide was stirred at ambient temperature for 17 hours. The reaction mixture was then added to an aqueous sodium bicarbonate solution and extracted with diethyl ether (2×). The combined organic layer was washed with water (3×) followed by a saturated sodium chloride solution, dried over anhydrous magnesium sulfate, and concentrated. The concentrate was triturated with hexane to afford 15.6 g (78%) of [N-methyl-N-(1H-pyrrol-1-yl)]-3-nitro-4-pyridinamine, m.p. 91°-99° C. Treatment of 5.0 of this product with ethereal hydrogen chloride yielded the corresponding hydrochloride salt. Recrystallization from isopropanol:-methanol (3:1) (2×) afforded 3.4 g of [N-methyl-N-(1H-pyrrol-1-yl)]-3-nitro-4-pyridinamine hydrochloride, mp 235°-236° C. (dec.).

ANALYSIS: Calculated for C$_{10}$H$_{10}$N$_4$O$_2$.HCl: 47.16% C, 4.35% H, 22.00% N. Found 47.07% C, 4.19% H, 22.09% N.

Step 5

Chilled dimethylformamide (5.5 ml) was treated with 7.5 ml of phosphorous oxychloride, stirred at ambient temperature ten minutes and then diluted with 10 ml of dichloroethane. The mixture was then treated with a solution of 12.0 g of [N-methyl-N-(1H-pyrrol-1-yl)]-3-nitro-4-pyridinamine (step 4) in 125 ml of dichloroethane. After stirring at 80° C. for four and one-half hours, the reaction mixture was quenched with a solution of 45 g of acetic acid, sodium salt trihydrate in 125 ml of water, refluxed at 80° C. for one hour, cooled, and diluted with 200 ml of dichloromethane. The organic layer was washed with an aqueous solution of sodium carbonate followed by a saturated sodium chloride solution, dried over anhydrous magnesium sulfate, filtered and concentrated to afford 7.3 g of 1-[-N-methyl-N-(3-nitro-4-pyridinyl)amino]pyrrole-2-carboxaldehyde, m.p. 101°-107° C., MS(EI)M+@ 247 (100%); IR(CHCl$_3$)—C=O @ 1680 cm$^{-1}$.

Step 6

To cold, concentrated hydrochloric acid (200 ml) was added, in the following order, 100 g of stannous chloride dihydrate, 200 ml of tetrahydrofuran, and a solution of 28 g of 1-[N-methyl-N-(3-nitro-4-pyridinyl)amino]pyrrole-2-carboxaldehyde in 150 ml of tetrahydrofuran. Upon completion of the 1-[N-methyl-N-(3-nitro-4-pyridinyl)amino]pyrrole-2-carboxaldehyde addition, the reaction was poured into an aqueous solution of sodium hydroxide (200 g in 1 liter of water), stirred for five minutes, and then extracted with ethyl acetate. The organic layer was washed with water followed by a saturated sodium chloride solution, dried over anhydrous magnesium sulfate, filtered, and concentrated. The resultant oil was purified by means of high pressure liquid chromatography (silica gel; elution with ethyl acetate) to afford 10 g (38%) of 5-methyl-5H-pyrido[3,4-f]pyrrolo[1,2-b][1,2,5]triazepine as an oil, IR(CHCl$_3$) C=N @ 1610 cm$^{-1}$; MS(EI)M+@ 199 (100%).

EXAMPLE 2

10,11-Dihydro-5-methyl-5H-pyrido[3,4-f]pyrrolo[1,2-b][1,2,5]triazepine

A solution of 4.2 g of 5-methyl-5H-pyrido[3,4-f]pyrrolo[1,2-b][1,2,5]triazepine in 75 ml of ethanol, was treated with 800 mg of sodium borohydride and stirred at ambient temperature for 18 hours. The solvent was then concentrated in vacuo and the residue taken up in water and extracted with ethyl acetate (2×). The combined organics were washed with water followed by a saturated sodium chloride solution, dried over anhydrous magnesium sulfate, filtered and concentrated. The resultant solid was recrystallized from isopropyl ether:methanol (180:10) to afford 3.1 g (74%) of 10,11-dihydro-5-methyl-5H-pyrido[3,4-f]pyrrolo[1,2-b][1,2,5]triazepine, m.p. 135°-140° C.

ANALYSIS: Calculated for C$_{11}$H$_{12}$N$_4$: 65.98% C, 6.04% H, 27.98% N. Found: 65.76% C, 6.18% H, 28.03% N.

EXAMPLE 3

10,11-Dihydro-5,10-dimethyl-5H-pyrido[3,4-f]pyrrolo[1,2-b][1,2,5]triazepine

To 8.4 ml of a solution of methyl magnesium iodide (3.2M in diethyl ether, diluted with 10 ml tetrahydrofuran) was added a solution of 4.1 g of 5-methyl-5H-pyrido[3,4-f]pyrrolo[1,2-b][1,2,5]triazepine in 70 ml of tetrahydrofuran. After stirring at ambient temperature for 20 hours, the reaction mixture was quenched into 200 ml of an iced ammonium chloride solution and extracted with ethyl acetate (2×). The combined organics were washed with water followed by a saturated sodium chloride solution and dried over anhydrous magnesium sulfate. The crude product was preadsorbed on silica (230-400 mesh) and flash chromatographed (elution with diethyl ether) to afford a solid, recrystallization of which from toluene yielded 2.1 g (48%) of 10,11-dihydro-5,10-dimethyl-5H-pyrido[3,4-f]pyrrolo[1,2-b][1,2,5]triazepine, mp 157°-160° C.

ANALYSIS: Calculated for $C_{12}H_{14}N_4$: 67.27% C, 6.59% H, 26.15% N. Found: 66.94% C, 6.73% H, 26.23% N.

EXAMPLE 4

10,11-Dihydro-5-methyl-10-phenyl-5H-pyrido[3,4-f]pyrrolo[1,2-b][1,2,5]triazepine To 15 ml of a 3M solution of phenyl magnesium bromide in ether diluted with 15 ml of tetrahydrofuran was added a solution of 4.45 g of 5-methyl-5H-pyrido[3,4-f]pyrrolo[1,2-b][1,2,5]triazepine in 75 ml of tetrahydrofuran. After stirring at ambient temperature for 45 minutes, the reaction mixture was quenched into an iced ammonium chloride solution. The aqueous layer was extracted with ethyl acetate (2×), and the combined organics were washed with water followed by a saturated sodium chloride solution, dried over anhydrous magnesium sulfate, filtered and concentrated. The resultant solid was purified via flash chromatography (compound preadsorbed on silica; elution with diethyl ether) and recrystallized from toluene to yield 4.0 g (64%) of 10,11-dihydro-5-methyl-10-phenyl-5H-pyrido[3,4-f]pyrrolo[1,2-b][1,2,5]triazepine, mp 200°-203° C.

ANALYSIS: Calculated for $C_{17}H_{16}N_4$: 73.89% C, 5.84% H, 20.27% N. Found: 73.91% C, 5.78% H, 20.12% N.

EXAMPLE 5

10,11-Dihydro-5-methyl-10-[(1-methyl)piperidin-4-yl]-5H-pyrido[3,4-f]pyrrolo[1,2-b][1,2,5]triazepine To a warm Grignard reagent prepared from 7.2 g of 4-chloro-1-methyl piperidine and 1.4 g of magnesium metal in 50 ml of tetrahydrofuran was added a solution of 5.3 g of 5-methyl-5H-pyrido[3,4-f]pyrrolo[1,2-b][1,2,5]triazepine in 50 ml of tetrahydrofuran. The reaction mixture was stirred at ambient temperature for 15 minutes, added to an iced ammonium chloride solution and extracted with ethyl acetate (3×). The combined organics were washed with water (2×) followed by a saturated sodium chloride solution, dried over anhydrous magnesium sulfate, filtered and concentrated. The resultant solid was purified by means of high pressure liquid chromatography (silica gel; elution with 50% methanol/dichloromethane). Recrystallization from ethyl acetate:methanol (20:1) afforded 1.65 g of 10,11-dihydro-5-methyl-10-[(1-methyl)piperidin-4-yl]-5H-pyrido[3,4-f]pyrrolo[1,2-b][1,2,5]triazepine, mp: 235°-238° C. (dec.).

ANALYSIS: Calculated for $C_{17}H_{23}N_5$: 68.66% C, 7.80% H, 23.55% N. Found: 68.46% C, 7.78% H, 23.49% N.

EXAMPLE 6

10,11-Dihydro-5-methyl-10-[3-(N,N-dimethylamino)-propyl]-5H-pyrido[3,4-f]pyrrolo[1,2-b][1,2,5]triazepine To magnesium turnings (1.4 g) in 10 ml of diether ether and 10 ml of tetrahydrofuran, was added a solution of 6.2 g of 3-(N,N-dimethylamino)propyl chloride in 10 ml of tetrahydrofuran. Initiation of the reaction was achieved by the addition of 1 ml of dibromoethane and the application of heat. After stirring at 70° C. for one hour, the reaction mixture was treated with a solution of 5.0 g of 5-methyl-5H-pyrido[3,4-f]pyrrolo[1,2-b][1,2,5]triazepine in 50 ml of tetrahydrofuran over a period of ten minutes. The reaction mixture was then stirred at 60° C. for thirty minutes, poured into 20 ml of an ammonium chloride solution (iced), stirred for five minutes, and extracted with ethyl acetate. The organic layer was washed with water followed by a saturated sodium chloride solution, dried over anhydrous magnesium sulfate, filtered and concentrated. The concentrate was purified by means of high pressure liquid chromatography (silica gel; elution with 50% methanol/dichloromethane) to afford 3.6 g (50%) of 10,11-dihydro-5-methyl-10-[3-(N,N-dimethylamino)propyl]-5H-pyrido-[3,4-f]pyrrolo[1,2-b][1,2,5]triazepine as an oil.

ANALYSIS: Calculated for $C_{16}H_{23}N_5$: 67.34% C, 8.12% H, 24.54% N. Found: 66.68% C, 8.43% H, 24.06% N.

EXAMPLE 7

11-Acetyl-10,11-dihydro-5-methyl-5H-pyrido[3,4-f]pyrrolo[1,2-b][1,2,5]triazepine maleate A mixture of 20 ml of acetic anhydride and 4.0 g of 10,11-dihydro-5-methyl-5H-pyrido[3,4-f]pyrrolo[1,2-b][1,2,5]triazepine was stirred at room temperature for two hours. The mixture was then evaporated, the residue dissolved in water, and the aqueous layer extracted with ethyl acetate. The organic layer was washed with water followed by a saturated sodium chloride solution, dried over anhydrous magnesium sulfate, filtered and concentrated. The concentrate was purified by means of high pressure liquid chromatography (silica gel; elution with ethyl acetate) to afford 2.3 g of 11-acetyl-10,11-dihydro-5-methyl-5H-pyrido[3,4-f]pyrrolo[1,2-b][1,2,5]triazepine as an oil which solidified upon standing (mp 125°-130° C.). The solid was dissolved in ethanol and acidified with an ethanol solution of maleic acid. Dilution with diethyl ether precipitated 2.25 g (31.4%) of the corresponding maleate, mp 139°-141° C.

ANALYSIS: Calculated for $C_{13}H_{14}N_4O \cdot C_4H_4O_4$: 56.98% C, 5.03% H, 15.64% N. Found: 56.75% C, 5.24% H, 15.43% N.

EXAMPLE 8

10,11-Dihydro-5-methyl-11-methylcarbamyl-5H-pyrido[3,4-f]pyrrolo[1,2-b][1,2,5]triazepine maleate A solution of 3.7 g of 10,11-dihydro-5-methyl-5H-pyrido[3,4-f]pyrrolo[1,2-b][1,2,5]triazepine in 100 ml of benzene was treated with 1.6 ml of methyl isocyanate and then stirred at 70° C. for five hours. After cooling, the mixture was evaporated under reduced pressure and the residue was dissolved in water. The aqueous layer extracted with ethyl acetate. The combined organic layer was washed with water followed by a saturated sodium chloride solution, dried over anhydrous magnesium sulfate, filtered and concentrated. Purification of the residue was achieved by means of high pressure liquid chromatography (silica gel; elution with 2.5% methanol/dichloromethane) to afford 2.3 g of 10,11-dihydro-5-methyl-11-methylcarbamyl-5H-pyrido[3,4-f]pyrrolo[1,2-b][1,2,5]triazepine m.p. 197°-200° C. (dec.). The solid was dissolved in ethanol and acidified with an ethanol solution of maleic acid to precipitate the corresponding maleate salt. Recrystallization of the salt from ethanol yielded 1.8 g of 10,11-dihydro-5-methyl-11-methylcarbamyl-5H-pyrido[3,4-f]pyrrolo[1,2-b][1,2,5]triazepine maleate, m.p. 160°–161° C.

ANALYSIS: Calculated for $C_{13}H_{15}N_5O.C_4H_4O_4$: 54.69% C, 5.09% H, 18.77% N. Found: 54.59% C, 5.23% H, 18.61% N.

EXAMPLE 9

10,11-Dihydro-5-methyl-10-(2-phenylethyl)-5H-pyrido[3,4-f]pyrrolo[1,2-b][1,2,5]triazepine To 2.8 g of magnesium turnings in 20 ml of diethyl ether and 20 ml of tetrahydrofuran was added 1 ml of 1,2-dibromoethane followed by 13.94 ml of 2-bromoethylbenzene (dropwise). After initiating the reaction with external heat, the mixture was stirred at room temperature for one hour and then treated, dropwise, with a solution of 10.0 g of 5-methyl-5H-pyrido[3,4-f]-pyrrolo[1,2-b][1,2,5]triazepine in 100 ml of tetrahydrofuran. The reaction mixture was then stirred at room temperature for two hours, poured into an iced ammonium chloride solution, stirred for five minutes, and extracted with ethyl acetate. The organic layer was washed with water followed by a saturated sodium chloride solution, dried over anhydrous magnesium sulfate, filtered and concentrated. The concentrate was purified by means of high pressure liquid chromatography (silica gel; elution with ethyl acetate). Flash chromatography of the resultant oil (silica gel; elution with 10% methanol/dichloromethane) afforded a solid which was recrystallized from diethyl ether/ethyl acetate (10:1) to yield 1.25 g of 10,11-dihydro-5-methyl-10-(2-phenylethyl)-5H-pyrido[3,4-f]pyrrolo[1,2-b][1,2,5]triazepine, mp 92°–94° C.

ANALYSIS: Calculated for $C_{19}H_{20}N_4$: 75.00% C, 6.58% H, 18.42% N. Found: 74.68% C, 6.72% H, 18.27% N.

EXAMPLE 10

10-[3-(N,N-Diethylamino)propyl]-10,11-dihydro-5-methyl-5H-pyrido[3,4-f]pyrrolo[1,2-b][1,2,5]triazepine sesquifumarate To magnesium turnings (1.9 g) in 10 ml of diethyl ether and 10 ml of tetrahydrofuran, was added a solution of 11.66 g of 3-diethylaminopropyl chloride in 10 ml of tetrahydrofuran. The reaction was initiated by the addition of 1 ml of dibromoethane and the application of heat. After stirring at 70° C. for four hours, the reaction mixture cooled to room temperature and treated, dropwise, with a solution of 7.7 g of 5-methyl-5H-pyrido[3,4-f]pyrrolo[1,2-b][1,2,5]triazepine in 50 ml of tetrahydrofuran. The mixture was then stirred at room temperature for two hours, poured into an iced ammonium chloride solution, and extracted with ethyl acetate (3×). The combined extracts were washed with water followed by a saturated sodium chloride solution, dried over anhydrous magnesium sulfate, filtered and concentrated. High pressure liquid chromatography of the concentrate (silica gel; elution with 15% methanol/dichloromethane) afforded 10-[3-(N,N-diethylamino)-propyl]-5-methyl-5H-pyrido[3,4-f]pyrrolo-[1,2-b][1,2,5]triazepine as an oil. The oil was dissolved in ethanol and acidified with an ethanol solution of fumaric acid. Diluting with diethyl ether precipitated 3.05 g of the corresponding sesquifumarate salt, mp 170°–172° C.

ANALYSIS: Calculated for $C_{18}H_{27}N_5.1.5C_4H_4O_4$: 59.14% C, 6.78% H, 14.37% N. Found: 58.84% C, 7.05% H, 14.09% N.

EXAMPLE 11

11-{1-[4-(2-methoxyphenyl)piperazin-1-yl]butyl}-10,11-dihydro-5-methyl-5H-pyrido[3,4-f]pyrrolo[1,2-b][1,2,5]triazepine To a slurry of 10% palladium on charcoal (2 g) in 5 ml ethanol was added a solution of 11-{1-[4-(2-methoxyphenyl)piperazin-1-yl)-2-butynyl}-10,11-dihydro-5-methyl-5H-pyrido[3,4-f]pyrrolo[1,2-b][1,2,5]triazepine (4.0 g) in 245 ml of ethanol. The resultant mixture was pressurized to 50 PSI with hydrogen then shaken on a Paar apparatus for four hours at room temperature. The mixture was then filtered and concentrated to an oil. Purification of the oil was accomplished by means of flash chromatography (silica gel; elution with 5% methanol/dichloromethane) to afford 1.4 g (35%) of 11-{1-[4-(2-methoxyphenyl)-piperazin-1-yl)-2-butyl}-10,11-dihydro-5-methyl-5H-pyrido[3,4-f]-pyrrolo[1,2-b][1,2,5]triazepine as an oil.

ANALYSIS: Calculated for $C_{26}H_{34}N_6O$: 69.96% C, 7.62% H, 18.83% N. Found: 69.54% C, 7.73% H, 18.45% N.

EXAMPLE 12

11-Formyl-10,11-dihydro-5-methyl-5H-pyrido[3,4-f]pyrrolo[1,2-b][1,2,5]triazepine maleate A mixture of 2.57 ml of acetic anhydride and 6.42 ml of formic acid was stirred at 60° C. for one hour. The reaction mixture was then cooled to room temperature and treated, dropwise, with a solution of 10,11-dihydro-5-methyl-5H-pyrido[3,4-f]pyrrolo[1,2-b][1,2,5]triazepine (3.5 g) in 50 ml of tetrahydrofuran. After stirring at room temperature for one hour, the mixture was then poured into water and treated with an aqueous solution of sodium bicarbonate until pH 8. The aqueous layer was extracted with ethyl acetate. The combined organics were washed with water followed by a saturated sodium chloride solution, dried over anhydrous magnesium sulfate, filtered and concentrated. The resultant solid was purified by means of high pressure liquid chromatography (silica gel; elution with ethyl acetate) to afford 3.2 g of a white solid, m.p. 133°–135° C. This material was converted to the maleate salt in ethanol to give 4.5 g of 11-Formyl-10,11-dihydro-5-methyl-5H-pyrido[3,4-f]pyrrolo[1,2-b]-[1,2,5]-triazepine maleate, m.p. 157°–159° C.

ANALYSIS: Calculated for: $C_{12}H_{12}N_4O.C_4H_4O_4$ 55.81% C, 4.65% H, 16.28% N. Found: 55.79% C, 4.74% H, 16.38% N.

EXAMPLE 13

11-[1-[4-(2-methoxyphenyl)piperazin-1-yl]-2-butynyl]-10,11-dihydro-5-methyl-5H-pyrido[3,4-f]pyrrolo-[1,2-b][1,2,5]triazepine Step 1

To a suspension of NaH (60% in oil, 1.0 g, 0.026 mole) in 10 ml of dry DMF at 0° C., was added a solution of 10,11-dihydro-5-methyl-5H-pyrido[3,4-f]pyrrolo[1,2-b][1,2,5]triazepine (4.6 g) in 50 ml of DMF.

After stirring at 0° C. for one hour, a solution of propargyl bromide (2.7 ml) in 10 ml of DMF was added, and the mixture was stirred at 0° C. for three hours, poured into 200 ml of water, stirred for five minutes, and then extracted with ethyl acetate. The organic layer was washed with water, and dried (saturated NaCl, anhydrous MgSO$_4$).

After filtration, the material was concentrated to 3.9 g of dark oil, which was eluted on a silica gel column with ethyl acetate via HPLC. The desired fraction was concentrated to 2.4 g of 11-(2-propynyl)-10,11-dihydro-5-methyl-5H-pyrido[3,4-f]pyrrolo[1,2-b][1,2,5]triazepine, as a light brown oil; MS(EI)M+@ 239 (100%), IR(CHCl$_3$)—C≡CH @ 3300 cm$^{-1}$.

Step 2

To 150 ml of p-dioxane were added 11-(2-propynyl)-10,11-dihydro-5-methyl-5H-pyrido[3,4-f]pyrrolo[1,2-b][1,2,5]triazepine (2.3 g), 4-(2-methoxyphenyl)piperazine (2.1 g), paraformaldehyde (2.0 g), and CuCl (0.02 g). After stirring at 80° C. for three hours, the mixture was concentrated to 6.9 g of brown oil, which was eluted on a silica gel column with 5% methanol/DCM via HPLC. The desired fraction was concentrated to 4.3 g of 11-[1-[4-(2-methoxyphenyl)piperazin-1-yl]-2-butynyl]-10,11-dihydro-5-methyl-5H-pyrido[3,4-f]pyrrolo[1,2-b][1,2,5]triazepine, as a light brown oil; MS(EI)M+@ 442 (6.7%), IR(CHCl$_3$)—C≡CH @ 3300 cm$^{-1}$.

EXAMPLE 14

10,11-Dihydro-10-oxo-5-methyl-5H-pyrido[3,4-f]pyrrolo[1,2-b][1,2,5]triazepine

Step 1

To a suspension of 10% Pd/C (1.7 g) in 50 ml of methanol, was added a solution of [N-methyl-N-(1H-pyrrol-1-yl)]-3-nitro-4-pyridinamine (15 g) in 200 ml of methanol. The mixture was shaken for four hours under 50 psi H$_2$ and filtered. The filtrate was concentrated to 12.8 g of 4-[N-methyl-N-(1H-pyrrol-1-yl)amino]-3-pyridinamine, MS(EI)M+@ 188 (100%), IR(CHCl-3)—NH$_2$ @ 3380 cm$^{-1}$ and 3470 cm$^{-1}$.

Step 2

To a solution of 4-[N-methyl-N-(1H-pyrrol-1-yl)amino]-3-pyridinamine (5.0 g) in 100 ml of DCM, was added ethyl chloroformate (7.7 ml). After stirring at ambient temperature for twenty hours, the solvent was evaporated to a brown oil, which was dissolved in water. The pH was adjusted to 10 with a Na$_2$CO$_3$ solution, and the product extracted with ethyl acetate. The organic layer was washed with water and dried (saturated NaCl, anhydrous MgSO$_4$). After filtering, the solvent was evaporated to 5.5 g of brown oil, which was eluted on a silica gel column with ethyl acetate via HPLC.

The desired fractions were combined and concentrated to 2.3 g of white solid, m.p. 143°-5° C.; 3-(N-ethoxycarbonyl)-4-[N-methyl-N-(1H-pyrrol-1-yl)amino]-3-pyridinamine. MS(EI)M+@ 260 (100%); IR(CHCl$_3$)—N—C═O @ 1730 cm$^{-1}$.

Step 3

To a solution of 3-(N-ethoxycarbonyl)-4-[N-methyl-N-(1H-pyrrol-1-yl)amino]-3-pyridinamine (1.4 g) in 30 ml of o-dichlorobenzene was added 4.7 g of fused ZnCl$_2$. After stirring at 160° C. for one hour, the solvent was decanted, and the dark residue was dissolved in water, pH was adjusted to 10 with Na$_2$CO$_3$ solution, and the product was extracted with ethyl acetate. The organic layer was washed with water and dried (saturated NaCl, anhydrous MgSO$_4$).

After filtering, the solvent was evaporated to 2.4 g of brown oil, which was eluted on a silica gel column with ethyl acetate via flash chromatography. The desired fractions were combined and concentrated to 0.2 g of tan solid, m.p. 175°-7° C., 10,11-dihydro-10-oxo-5-methyl-5H-pyrido[3,4-f]pyrrolo[1,2-b][1,2,5]triazepine. MS(EI)M+@ 214 (100%); IR(CHCl$_3$)—N—C═O @ 1660 cm$^{-1}$.

What is claimed is:

1. A pharmaceutical composition which comprises an effective memory enhancing amount of a compound of the formula:

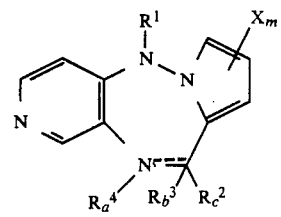

wherein $R^1$ is loweralkyl, arylloweralkyl, or aminoloweralkyl; $R^2$ is hydrogen, loweralkyl, arylloweralkyl, aminoloweralkyl, aryl or a group of the formula

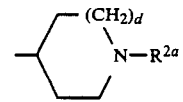

wherein d is an integer having a value of zero or 1 and $R^{2a}$ is hydrogen, loweralkyl, arylloweralkyl or aminoloweralkyl; $R^3$ is hydrogen or loweralkyl, or together with $R^2$ constitutes a radical of the formula═O; $R^4$ is hydrogen, loweralkyl, arylloweralkyl, aminoloweralkyl, formyl, loweralkylcarbonyl, aminocarbonyl, arylaminocarbonyl, or a group of the formula

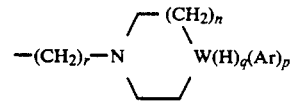

wherein W is carbon or nitrogen, Ar is aryl, q is an integer having a value from zero to 2, inclusive, p is an integer having a value of zero or 1, with the proviso that the sum of p and q is 1 when W is nitrogen and 2 when W is carbon, n is an integer having a value of zero or 1, and r is an integer having a value from 2 to 4, inclusive; X is halogen, loweralkyl, loweralkenyl, formyl or loweralkanol; m is an integer having a value of zero or 1; the dotted line is an optional bond; and a, b, and c, are integers having values of zero or one with the proviso that in the presence of said optional bond a is zero and the sum of b plus c is one, and in the absence of said optional bond a, b, and c each have a value of 1; and a suitable carrier therefor.

2. A method of treating a patient in need of memory enhancement which comprises administering to the patient an effective memory-enhancing amount of a compound of the formula:

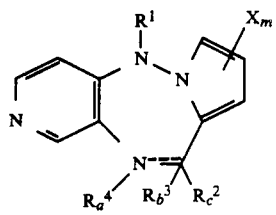

wherein $R^1$ is loweralkyl, arylloweralkyl, or aminoloweralkyl; $R^2$ is hydrogen, loweralkyl, arylloweralkyl, aminoloweralkyl, aryl or a group of the formula

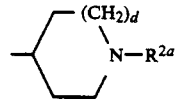

wherein d is an integer having a value of zero or 1 and $R^{2a}$ is hydrogen, loweralkyl, arylloweralkyl or aminoloweralkyl; $R^3$ is hydrogen or loweralkyl, or together with $R^2$ constitutes a radical of the formula=O; $R^4$ is hydrogen, loweralkyl, arylloweralkyl, aminoloweralkyl, formyl, loweralkylcarbonyl, aminocarbonyl, arylaminocarbonyl, or a group of the formula $$-(CH_2)_r-N\underset{\diagdown \diagup}{\overset{\diagup (CH_2)_n \diagdown}{}}W(H)_q(Ar)_p$$

wherein W is carbon or nitrogen, Ar is aryl, q is an integer having a value from zero to 2, inclusive, p is an integer having a value of zero or 1, with the proviso that the sum of p and q is 1 when W is nitrogen and 2 when W is carbon, n is an integer having a value of zero or 1, and r is an integer having a value from 2 to 4, inclusive; X is halogen, loweralkyl, loweralkenyl, formyl or loweralkanol; m is an integer having a value of zero or 1; the dotted line is an optional bond; and a, b, and c, are integers having values of zero or one with the proviso that in the presence of said optional bond a is zero and the sum of b plus c is one, and in the absence of said optional bond a, b, and c each have a value of 1.

3. A pharmaceutical composition which comprises an effective depression alleviating amount of a compound of the formula:

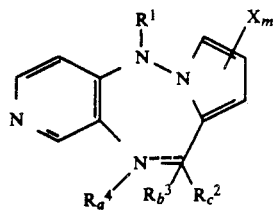

wherein $R^1$ is loweralkyl, arylloweralkyl, or aminoloweralkyl; $R^2$ is hydrogen, loweralkyl, arylloweralkyl, aminoloweralkyl, aryl or a group of the formula

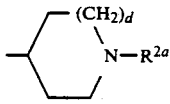

wherein d is an integer having a value of zero or 1 and $R^{2a}$ is hydrogen, loweralkyl, arylloweralkyl or aminoloweralkyl; $R^3$ is hydrogen or loweralkyl, or together with $R^2$ constitutes a radical of the formula=O; $R^4$ is hydrogen, loweralkyl, arylloweralkyl, aminoloweralkyl, formyl, loweralkylcarbonyl, aminocarbonyl, arylaminocarbonyl, or a group of the formula

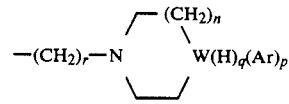

wherein W is carbon or nitrogen, Ar is aryl, q is an integer having a value from zero to 2, inclusive, p is an integer having a value of zero or 1, with the proviso that the sum of p and q is 1 when W is nitrogen and 2 when W is carbon, n is an integer having a value of zero or 1, and r is an integer having a value from 2 to 4, inclusive; X is halogen, loweralkyl, loweralkenyl, formyl or loweralkanol; m is an integer having a value of zero or 1; the dotted line is an optional bond; and a, b, and c, are integers having values of zero or one with the proviso that in the presence of said optional bond a is zero and the sum of b plus c is one, and in the absence of said optional bond a, b, and c each have a value of 1; and a suitable carrier therefor.

4. A method of treating a patient in need of relief from depression which comprises administering to the patient an effective depression-alleviating amount of a compound of the formula:

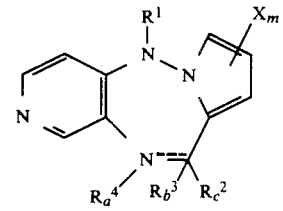

wherein $R^1$ is loweralkyl, arylloweralkyl, or aminoloweralkyl; $R^2$ is hydrogen, loweralkyl, arylloweralkyl, aminoloweralkyl, aryl or a group of the formula

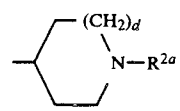

wherein d is an integer having a value of zero or 1 and $R^{2a}$ is hydrogen, loweralkyl, arylloweralkyl or aminoloweralkyl; $R^3$ is hydrogen or loweralkyl, or together with $R^2$ constitutes a radical of the formula=O; $R^4$ is hydrogen, loweralkyl, arylloweralkyl, aminoloweralkyl, formyl, loweralkylcarbonyl, aminocarbonyl, arylaminocarbonyl, or a group of the formula

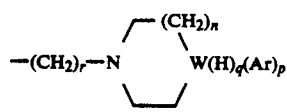

wherein W is carbon or nitrogen, Ar is aryl, q is an integer having a value from zero to 2, inclusive, p is an integer having a value of zero or 1, with the proviso that the sum of p and q is 1 when W is nitrogen and 2 when W is carbon, n is an integer having a value of zero or 1, and r is an integer having a value from 2 to 4, inclusive; X is halogen, loweralkyl, loweralkenyl, formyl or loweralkanol; m is an integer having a value of zero or 1; the dotted line is an optional bond; and a, b, and c, are integers having values of zero or one with the proviso that in the presence of said optional bond a is zero and the sum of b plus c is one, and in the absence of said optional bond a, b, and c each have a value of 1.

* * * * *